United States Patent [19]
Sandoz et al.

[11] Patent Number: 5,897,994
[45] Date of Patent: Apr. 27, 1999

[54] FATTY ACID FRACTIONATION FOR POLYUNSATURATED FATTY ACID FRACTION ENRICHMENT

[75] Inventors: Laurence Sandoz, Servion; Hans-Juergen Wille, Villeneuve, both of Switzerland

[73] Assignee: Nestec S.A., Vevey, Switzerland

[21] Appl. No.: 08/642,338

[22] Filed: May 3, 1996

[30] Foreign Application Priority Data

May 4, 1995 [EP] European Pat. Off. ............. 95201151

[51] Int. Cl.$^6$ .................................. C12P 7/64; C11C 1/00
[52] U.S. Cl. ........................ 435/134; 435/135; 435/271; 435/198; 435/136
[58] Field of Search ..................................... 435/134, 135, 435/136, 911, 198, 271

[56] References Cited

U.S. PATENT DOCUMENTS 4,275,081  6/1981  Coleman et al. .......................... 426/33
4,776,984  10/1988  Traitler et al. .

FOREIGN PATENT DOCUMENTS 4124517  1/1993  Germany .

OTHER PUBLICATIONS

Langholz et al., J. Am.Oil. Chem. Soc., vol. 66, 1989, pp. 1120–1123.

Kirk–Othmer Encyclopedia of Chemical Technology, vol. 21, Third edition, 1984.

Syed, et al., Enrichment of γ–Linolenic Acid From Evening Primrose Oil and Borage Oil Via Lipose–Catalyzed Hydroiysis. Journal of the American Oil Chemists Society, vol. 71, No. 6, 1994, pp. 563–567, and.

Syed et al., Y–Linolenic Acid Concentrates From Borage and Evening Primrose Oil Fatty Acids Via Lipose–Catalyzed Esterification Journal of the American Oil Chemists Society, vol. 71, No. 6, 1994, pp. 569–573.

Huge–Jensen, et al. Studies on Free and Immobilized Lipases from Mucor Miehei, Jaocs, vol. 65, No. 6 (1988); and.

Hills, Matthew, J. et al, Enzymatic Fractionation of Fatty Acids: Enrichment of Y–Linolenic Acid and Docosahexaenoic Acid by Selective Esderification Catalyzed by Lipases, Jaocs, vol. 67, No. 9 (Sep. 1990).

*Primary Examiner*—Irene Marx
*Attorney, Agent, or Firm*—Vogt & O'Donnell, LLP

[57] ABSTRACT

A mixture of fatty acids rich in polyunsaturated fatty acids is esterified by enzymatic catalysis and then the reaction mixture is saponified, which provides an organic phase containing esters and an aqueous phase which contains fatty acids, the phases are separated and the fatty acids of the aqueous phase are extracted by a non-polar solvent to obtain the fatty acids in the solvent, after which the solvent may be removed from the fatty acids.

19 Claims, No Drawings

FATTY ACID FRACTIONATION FOR POLYUNSATURATED FATTY ACID FRACTION ENRICHMENT

BACKGROUND OF THE INVENTION

The present invention relates to fatty acid fractionation for polyunsaturated fatty acid fraction enrichment, and the present invention also relates to employing enzymatic hydrolysis and enzymatic esterification in the course of obtaining the fractions.

Fatty acids of the n-6 and n-3 series have a nutritional value, in particular as precursors in the biosynthesis of prostaglandins. It may be advantageous to have available fractions enriched in these fatty acids for various nutritional and cosmetic applications. These fatty acids are found in nature principally in the form of triglycerides. Free fatty acids are obtained industrially from triglycerides by hydrolysis at a high temperature and under a high pressure. In order then to fractionate these fatty acids, several methods have been developed, for example crystallization, distillation, the formation of inclusion complexes or chromatographic techniques. Application of these methods may bring about degradation in the case of polyunsaturated fatty acids or prove to be too costly to be applied industrially.

Enzymatic methods represent an alternative to the preceding methods since they enable reactions to be carried out under mild conditions using little energy and equipment which is less stressed.

Enzymatic processes are known, for example from Matthew J. Hills et al in JAOCS, Vol.67, no.9, p.561–563, for fractionating fish oil and evening primrose oil fatty acids based on the fact that the kinetics of the esterification by butanol catalysed by rape lipases and *Mucor miehei* would be a function of the degree of saturation of the acid to be esterified. After esterification of fatty acids with a higher degree of saturation, the esters are separated from the fatty acids which have not reacted, by thin layer chromatography.

SUMMARY OF THE INVENTION

The object of the invention is to provide a process for the fractionation of fatty acids from oils rich in polyunsaturated fatty acids by enzymatic esterification which is applicable industrially, avoiding chromatographic separation.

The invention thus concerns an essentially enzymatic process for the fractionation of polyunsaturated fatty acids, in which esterification of a mixture of fatty acids is carried out by enzymatic catalysis, the esters formed are then separated from the fatty acids which have not reacted and a fraction is obtained enriched in the desired polyunsaturated fatty acids, characterized in that the esters of the fatty acids are separated by controlled saponification of the fatty acids, extraction of the soaps formed with water, acidification of the aqueous phase and extraction of the acids formed with a non-polar solvent.

DETAILED DESCRIPTION OF THE INVENTION

In order to put the process according to the invention into practice, the mixture of fatty acids used is derived, preferably, from the total enzymatic hydrolysis of the triglycerides of an oil rich in polyunsaturated fatty acids. This hydrolysis preferably takes place in a medium emulsified by a non regio-specific lipase of *Candida cylindracea*, preferably at room temperature, at neutral pH or close to neutrality and at atmospheric pressure.

As the starting oil, any natural oil may be cited of animal or vegetable or synthetic origin containing polyunsaturated fatty acids, in particular with a degree of unsaturation of three and more, including fatty acids of the n-3 and n-6 series, for example blackcurrant seed oil, borage oil, evening primrose oil, rich in gamma-linolenic acid (GLA), or "TGA" oil rich in arachidonic acid.

Esterification takes place in the presence of methanol and a solvent, for example hexane or a small quantity of water. The reaction lasts 5 to 70 h and preferably 10 to 40 h, preferably at room temperature. The enzyme used may be immobilized or not. It is preferably immobilized so that it can be reused. It may be regio-specific or not.

After reaction, a mixture is obtained of free fatty acids and the methyl esters of fatty acids. The esterified fraction is impoverished in fatty acids with a high degree of unsaturation, for example in the case of blackcurrant seed oil particularly in GLA and in stearidonic acid (SA), which indicates that these acids are hardly esterified at all and consequently enriched in the free fatty acids fraction.

According to the invention, separation of free fatty acids from the esters takes place by saponification of fatty acids under mild conditions. These conditions are characterized by a reaction with a weak base in an aqueous medium, for example carbonates, phosphates, citrates of sodium, potassium or ammonium or their mixtures, preferably sodium carbonate, at a temperature starting from room temperature, for example 20° C. up to about 80° C., with stirring and preferably increasing stirring and progressively the temperature from 45° C. up to about 75° C. Separation is then observed between an aqueous phase and an organic phase and this separation can be accentuated, for example by addition of a saturated solution of sodium chloride.

It is possible by this process to react only the fatty acids which, in the form of soaps, become water soluble. The aqueous phase obtained can be then separated easily from the organic phase containing the liposoluble esters after decantation, for example by centrifuging. The free fatty acids can be recovered by acidification of the aqueous phase by an acid, for example concentrated hydrochloric acid, extracted by a solvent, for example hexane, and the solvent can then be removed, for example by evaporation.

EXAMPLES

The following examples illustrate the invention. In these, the percentages and parts are by weight, unless indicated to the contrary. As regards the quantitative analysis of free fatty acids, this was carried out, following methylation by acetyl chloride, by gaseous phase chromatography (GPC), and thus on the basis of the methyl esters.

Example 1

1.1. Preparation of the starting mixture of fatty acids.

A mixture of fatty acids was used as starting material derived from the enzymatic hydrolysis of a blackcurrant seed oil by means of a nonspecific lipase of *Candida cylindracea*.

To obtain the mixture of fatty acids, and oil-in-water emulsion was prepared containing 20% of blackcurrant seed oil and 1.2% of soya lecithin (ASOL 100 Lucas Meyer) dissolved in 78.8% of an aqueous solution 20 of 0.025M phosphate buffer of pH 6.88 and carrying out 5 passes through a microfluidizer (110T, Microfluidics Corporation, Newton), which led to a mean diameter of the oil droplets of about 450 nm.

Lipase of *Candida cylindracea* type B, Biocatalysts Ltd., Cardiff, England, was solubilized in the phosphate buffer, and then centrifuged at 4000 g for 20 min. to remove the insoluble residues. The supernatant was used for the experiments. 10 ml of the preceding emulsion (containing 2 g of blackcurrant seed oil) were placed in a 25 ml stoppered Erlenmeyer flask, in a bath thermostatically controlled to a temperature of 37° C. with magnetic stirring at 250 rpm to which the enzyme solution was added corresponding to 0.2 g of lipase.

After reacting for 4 h, the medium was centrifuged at 4000 g to break the emulsion and the lipid phase was recovered by extraction with ether. The extract was washed with water and dried over sodium sulphate, and the solvent then was eliminated by evaporation. The fatty acids obtained were stored at −25° C. protected from the light and under nitrogen.

The lipase in solution in the aqueous phase was recovered as well as the glycerol formed by ultrafiltration (module YM 10, cut off threshold 10,000, Amicon, Denver, U.S.A.), which gave a concentrated solution of lipase which could be reused.

The degree of hydrolysis, corresponding to the percentage of fatty acids liberated during the reaction corresponded to 99.9%, determined by acid-base titration with the aid of a Metrohm titroprocessor 692. The sample to be analysed, dissolved in 25 ml of an equivolume mixture of ethanol and ethyl ether, was titrated with an alcoholic solution of KOH with a concentration of 0.1N.

The mixture of fatty acids had the following composition determined by GPC in the form of methyl esters

| Fatty Acids | % |
| --- | --- |
| C 16:0 | 7.1 |
| C 18:0 | 1.7 |
| C 18:1 | 13.3 |
| C 18:2 | 45.6 |
| C 18:3 gamma | 15.5 |
| C 18:3 alpha | 12.2 |
| C 18:4 | 2.9 |
| C 20:1 | 0.8 |
| C 20:2 | 0.2 |
| Others | 0.8 |

1.2 Esterification

The fatty acids were esterified by methanol using 900 mg of the mixture of fatty acids in a mixture of 11 ml of hexane and 1 ml of methanol and 1200 mg of immobilised enzyme, Lipozyme TM 20 from *Mucor miehei,* Novo Nordisk, A/S Denmark. This enzyme has an increased specificity for positions 1 and 3 of the glycerol skeleton of the triglycerides compared with position 2. The reaction was carried out at room temperature in a glass flask provided with a magnetic bar and placed on a mechanical stirrer for 20 h. After reaction, the enzyme was filtered off which, after rinsing and rehydration with 10% water by volume, could be reused. A mixture of free fatty acids and methyl esters of fatty acids was obtained.

1.3. Separation of fatty acids and methyl esters.

20 g of the preceding mixture of fatty acids and fatty acid methyl esters were heated at 40° C., and then 1.1 g of sodium carbonate dissolved in water was added with stirring. The rate of stirring was then increased and the temperature raised to 75° C. When this latter temperature was reached, heating was discontinued and 20 ml of saturated salt solution was added. The formation of an organic phase and an aqueous phase was then noted. Everything was then centrifuged for 10 min at 3000 rpm, two phases were separated and the aqueous phase which contained soaps was then acidified with a solution of hydrochloric acid. The fatty acids formed were then extracted with hexane and the hexane was then evaporated off. 1.5 g of fatty acids were thus recovered enriched in GLA and in SA having the following composition (GPC of methyl esters):

| Fatty Acids | % |
| --- | --- |
| C 16:0 | 1.3 |
| C 18:1 | 2 |
| C 18:2 | 6.5 |
| C 18:3 gamma | 73.4 |
| C 18:3 alpha | 2.4 |
| C 18:4 | 13.6 |
| Others | 0.8 |

Example 2

The procedure was as in example 1, except that in the esterification stage (corresponding to 1.2 of example 1), a mixture of solvents was used consisting of 9 ml of methanol and 1 ml of water.

64.6% of GLA and 11.8% of SA were thus obtained in the enriched phase (consisting of the non-esterified part obtained from the soaps).

Examples 3–7

The procedure was as in example 1, except for the fact that, in the esterification stage (corresponding to 1.2 in example 1), the enzyme reaction time was varied as indicated, and with the results of the % GLA and SA in the enriched phase indicated below (determined by GPC of the methyl esters):

| Example | 3 | 4 | 5 | 6 | 7 |
| --- | --- | --- | --- | --- | --- |
| Reaction time, h | 5 | 10 | 30 | 40 | 70 |
| % GLA | 70 | 73.5 | 77.6 | 75.6 | 74.8 |
| % SA | 12 | 13 | 12.6 | 13.3 | 12.8 |

Examples 8–15

The esterification of a mixture of blackcurrant seed oil fatty acids was carried out as in example 1 (corresponding to 1.2 of example 1) with enzymes of various origins and regio-specificities by reaction at room temperature for 20 h. The results obtained were evaluated by determining the composition in fatty acids of the esterified fraction (by GPC in the form of methyl esters):

|  | Example | | | | | | | |
|---|---|---|---|---|---|---|---|---|
|  | 8 | 9 | 10 | 11 | 12 | 13 | 14 | 15 |
|  | Enzyme of | | | | | | | |
|  | Rhizopus javanicus Bio-catalyst | Penicillium cyclopium | Penicillium roqueforti | Geotrichum candidum | Lipomod mixture of lipases | Candida cylindracea TYPE OF | Rhizopus javanicus, Type F-AP 15 | Aspergilus niger type AP 6 |
| C 13:0 | — | — | — | 0.5 | — | — | — | — |
| C 16:0 | 7.6 | 5.8 | 8.8 | 11.2 | 8.4 | 7.9 | 8.1 | 7.6 |
| C 16:1 | — | 0.1 | — | — | — | — | — | — |
| C 18:0 | 1.2 | 1.1 | 1.8 | 1.8 | 1.5 | 1.4 | 1.3 | 1.4 |
| C 18:1 | 15.8 | 15.7 | 16.3 | 12.8 | 16.9 | 15.9 | 15.4 | 17.4 |
| C 18:2 | 57 | 59 | 54.9 | 48.7 | 56.8 | 56.2 | 56.1 | 57.7 |
| C 18:3 gamma | 2.1 | 1.6 | 2.2 | 1.2 | 1.8 | 2 | 5.1 | 2 |
| C 18:3 alpha | 14.5 | 15.3 | 13.5 | 7.2 | 12.3 | 14.4 | 12.9 | 13 |
| C 18:4 | — | — | — | 1.8 | 1 | 0.3 | — | — |
| C 20:1 | 0.6 | 0.6 | 0.8 | 0.6 | — | 0.8 | 0.6 | 0.8 |
| C 20:2 | — | 0.2 | — | — | — | 0.2 | — | — |
| Others | 1.3 | 0.6 | 1.8 | 14.2 | 1.4 | 0.8 | 0.5 | 0.1 |

—: not quantifiable

As may be seen from the Table for Examples 8–15, and as may be seen from the preceding descriptions of Examples 1–7, a mixture of unsaturated fatty acids, which comprise mono-unsaturated, di-unsaturated and polyunsaturated fatty acids, is esterified in the presence of methanol with a lipase which is suitable for esterifying mono- and di-unsaturated fatty acids so that a reaction product of mono- and di-unsaturated fatty acid methyl esters and of free polyunsaturated fatty acids is obtained, and after addition of a weak base to the reaction product, a second reaction product is obtained which comprises an aqueous fraction phase and an ester fraction phase. The tabular results of Examples 8–15 show that in all cases the esterified fraction was impoverished in GLA and in SA, which indicates that these two acids were hardly esterified at all and hence that the free fatty acids fraction was enriched in these acids.

Example 16

As a raw material, use was made of a total hydrolysate of a synthetic TGA oil from Suntory Ltd. Tokyo, Japan, extracted from *Mortierella fungus*, very rich in arachidonic acid. After hydrolysis of the triglycerides, the mixture of free fatty acids was esterified as in example 1 (corresponding to 1.2 of Example 1) with LIPOZYME 20 for 20 h at room temperature. The methyl esters of the free fatty acids were then separated by thin layer chromatography, and the composition of the mixture of free fatty acids was then analysed. The composition of the starting mixture of fatty acids and that of the mixture of free fatty acids obtained after esterification (determined by GPC of the methyl esters) are indicated below:

| Composition of fatty acids % | Of the TGA oil | Of the esterified fraction |
|---|---|---|
| C 14:0 | 0.7 | — |
| C 16:0 | 17.2 | 5.6 |
| C 16:1 | 0.2 | — |
| C 17:0 | 0.3 | 0.2 |
| C 18:0 | 9.2 | 5.5 |
| C 18:1 | 22.3 | 7.7 |
| C 18:2 | 8.3 | 2.4 |
| C 18:3 gamma | 1.7 | 6.5 |
| C 18:3 alpha | 1 | — |
| C 20:0 | 0.9 | 0.9 |
| C 20:1 | 1 | 0.7 |
| C 20:2 | 0.7 | 0.5 |
| C 20:3 | 3.9 | 13.1 |
| C 20:4 | 20.2 | 40.2 |
| C 22:0 | 3.5 | 4.2 |
| C 22:6 | 8.2 | 11.2 |
| Others | 0.7 | 1.5 |

—: not quantifiable

The preceding results show that, as for blackcurrant seed oil, it was especially the fatty acids that were tri-unsaturated which were more enriched in the free fatty acid fraction. It will also be noted that, in spite of its low percentage of TGA oil, GLA was selectively enriched relative to alpha linolenic acid (ALA).

We claim:

1. A process for fractionating unsaturated fatty acids comprising polyunsaturated fatty acids for obtaining a fatty acid fraction enriched in polyunsaturated fatty acids comprising:

esterifying a mixture of unsaturated fatty acids in the presence of methanol, wherein the fatty acid mixture comprises fatty acids selected from the group consisting of mono-unsaturated, di-unsaturated and polyunsaturated fatty acids, with a lipase suitable for esterifying mono-unsaturated and di-unsaturated fatty acids to obtain a first reaction product comprising mono- and di-unsaturated fatty acid methyl esters and free polyunsaturated fatty acids;

adding to and reacting with the first reaction product a weak base to obtain a second reaction product comprising an aqueous fraction phase which comprises salts of the free polyunsaturated fatty acids and comprising an ester fraction phase which comprises the mono- and di-unsaturated fatty acid methyl esters;

separating the ester fraction phase from the aqueous fraction phase to obtain the aqueous fraction phase;

acidifying the aqueous fraction phase to obtain free polyunsaturated fatty acids in an acidified aqueous medium; and extracting the free polyunsaturated fatty acids from the acidified aqueous medium with a non-polar solvent to obtain the free polyunsaturated fatty acids in the solvent.

2. A process according to claim 1 further comprising removing the solvent from the fatty acids.

3. A process according to claim 2 wherein the solvent is evaporated for removing the solvent.

4. A process according to claim 1 wherein the solvent is hexane.

5. A process according to claim 1 wherein the aqueous fraction and ester fraction phases are centrifuged for separating the phases.

6. A process according to claim 5 wherein the acid is hydrochloric acid.

7. A process according to claim 5 wherein the acid is concentrated hydrochloric acid.

8. A process according to claim 1 wherein the acid is hydrochloric acid.

9. A process according to claim 1 wherein the acid is concentrated hydrochloric acid.

10. A process according to claim 1 further comprising, after adding the weak base to the first reaction product, adding also a saturated sodium chloride solution to obtain the second reaction product.

11. A process according to claim 1 wherein the base is selected from the group consisting of sodium carbonate, potassium carbonate, ammonium carbonate, sodium phosphate, potassium phosphate, ammonium phosphate, sodium citrate, potassium citrate, ammonium citrate and mixtures thereof.

12. A process according to claim 1 wherein the weak base is sodium carbonate.

13. A process according to claim 1 further comprising, after adding the weak base to the first reaction product, also stirring and heating to a temperature of up to 80° C. to react the weak base and first reaction product to obtain the second reaction product.

14. A process according to claim 1 wherein the heating is at a temperature of from about 45° C. to about 75° C.

15. A process according to claim 1 wherein the fatty acid mixture comprises n-3 and n-6 series fatty acids.

16. A process according to claim 1 wherein the fatty acid mixture comprises fatty acids selected from the group consisting of gamma-linolenic acid, stearidonic acid and mixtures thereof.

17. A process according to claim 1 wherein the fatty acid mixture comprises fatty acids of an oil selected from the group consisting of blackcurrant seed oil, borage oil and evening primrose oil.

18. A process according to claim 1 wherein the fatty acid mixture is esterified with a regio-specific lipase.

19. A process according to claim 1 wherein the fatty acid mixture is esterified with a lipase from *Mucor miehei*.

* * * * *